United States Patent [19]

Sato et al.

[11] Patent Number: 4,642,409

[45] Date of Patent: Feb. 10, 1987

[54] METHOD FOR SELECTIVE DEALKYLATION OF A DIALKYLBENZENE AT THE PARAPOSITION THEREOF

[75] Inventors: Hiroshi Sato; Norio Ishii; Kenichi Hirose, all of Osaka, Japan

[73] Assignee: Sumitomo Chemical Company, Limited, Osaka, Japan

[21] Appl. No.: 827,698

[22] Filed: Feb. 10, 1986

[51] Int. Cl.$^4$ .............................................. C07C 4/12
[52] U.S. Cl. ...................................... 585/486; 585/489
[58] Field of Search ................................ 585/486, 489

[56] References Cited

U.S. PATENT DOCUMENTS 4,181,811 1/1980 Young ................................ 585/486
4,205,189 5/1980 Young et al. ...................... 585/481
4,499,321 2/1985 Sato et al. ......................... 585/486

Primary Examiner—Curtis R. Davis
Attorney, Agent, or Firm—Sughrue, Mion, Zinn, Macpeak and Seas

[57] ABSTRACT

An industrially excellent method for selectively dealkylating a 1,4-dialkylbenzene in a dialkylbenzene mixture by the use of a specified zeolite catalyst is disclosed, which catalyst is a crystalline zeolite ion-exchanged with sodium ion, potassium ion, potassium ion, rubidium ion, or cesium ion. The specific zeolite catalyst is easy to prepare and allows selective dealkylation of the 1,4-dialkylbenzene and recovery of the formed olefins in a high yield and a high purity.

7 Claims, No Drawings

METHOD FOR SELECTIVE DEALKYLATION OF A DIALKYLBENZENE AT THE PARAPOSITION THEREOF

FIELD OF THE INVENTION

The present invention relates to a method for selectively dealkylating a dialkylbenzene at the paraposition thereof. More particularly, the present invention is intended, by dealkylating a 1,4-dialkylbenzene in a dialkylbenzene mixture by a shape-selective reaction using a specified zeolite catalyst, to remove the 1,4-dialkylbenzene from the mixture or reduce the 1,4-dialkylbenzene concentration of the mixture, whereby the side reactions (e.g., oligomerization, cracking, etc.) of an olefin produced by the dealkylation are suppressed, and the percent recovery and purity of the eliminated olefin are kept at a high level to facilitate the reuse of the olefin and improve the economy of the dealkylation.

BACKGROUND OF THE INVENTION

Generally, dialkylbenzenes obtained by the dealkylation of benzenes are a mixture of 1,2-, 1,3-, and 1,4-isomers, but a difference in boiling point between these isomers is so small that, in many cases, even rectifying columns having many plates are insufficient to separate these isomers from one another by distillation.

Next, one specific example will be given. Cymene isomers obtained by the alkylation of toluene with propylene have the following boiling points: o-Isomer, 178.3° C.; m-isomer, 175.1° C.; and p-isomer, 177.1° C. A difference in boiling point between m- and p-cymenes, which comes into special question in the cresol manufacturing process, is only 2° C., so that separation of the both by rectification is extremely difficult. In the cresol manufacturing process now in use, therefore, the following procedure is employed: The mixed cymene, without being separated into the isomers, is oxidized as such into a mixed cresol, and thereafter, separation of the cresol isomers is carried out.

As one method to separate the cresol isomers from one another, there is a method in which the cresol mixture is alkylated with isobutylene into a mixture of tert-butyl cresol isomers, the isomers are separated from one another by rectification taking advantage of a large difference in boiling point between them, and then the tertiary butyl group is eliminated to obtain high-purity m- and p-cresols.

As another method to separate the cresol isomers from one another, there is a method in which a mixture of cresol urea isomeric clathrate compounds is separated into the isomers by recrystallization taking advantage of a difference in crstallizability between them, and the separated compounds are decomposed to obtain high-purity m- and p-cresols.

The foregoing both methods are a separation method now in use in industry, but their process is so complicated that a furthermore improvement is desired.

Another specific example will be given below. Diisopropylbenzene obtained by the alkylation of benzene, which is a starting material for 1,3-dihydroxybenzene (resorcinol) and 1,4-dihydroxybenzene (hydroquinone), comprises the isomers having the following boiling points: o-Isomer, 200° C.; m-isomer, 203.2° C.; and p-isomer, 210.3° C. A difference in boiling point between m- and p-diisopropylbenzenes, which comes into special question in the resorcinol and hydroquinone manufacturing process, is 7° C., so that separation of the both by rectification is possible. This method, however, requires rectifying columns having a fairly large number of plates so that it may not always be said to be a separation method of good efficiency.

Instead of these conventional separation methods, there are proposed ones based on a new idea which are intended to selectively dealkylate only the 1,4-dialkyl isomer in the dialkylbenzene, to thereby recover the 1,3-dialkyl isomer (in some cases, 1,2- plus 1,3-dialkyl isomers) as unreacted (Japanese Patent Application (OPI) Nos. 83716/1980 and 83721/1980). (The term "OPI" as used herein refers to a "published unexamined Japanese patent application", hereinafter the same.) This method uses a ZSM type zeolite as a catalyst, and particularly, a ZSM type zeolite catalyst modified with oxides such as MgO, $P_2O_5$, etc., dealkylates only the 1,4-dialkyl isomer with a very high selectivity, so that this method is a markedly epoch-making technique.

From the practical point of view, however, this method also has a large defect that, when the alkyl group to be dealkylated has three or more carbon atoms, olefins obtained by the dealkylation are low in purity and percent recovery. For example, Example 10 of Japanese Patent Application (OPI) No. 83716/1980 discloses that m-cymene is obtained in a high purity (96.6%) by dealkylating a mixed cymene (o/m/p=2.16/66.16/31.67) using a steam-treated H-ZSM-5, but the purity of propylene recovered at that time is about 60% in the volatile gas obtained. Similarly, Example 11 of Japanese Patent Application (OPI) No. 83721/1980 discloses that a high-purity m-cymene is obtained by dealkylating a mixed cymene using a similar catalyst, but the purity of propylene recovered at that time is 43%. When these known methods were verified by the present inventors, many kinds of $C_2$–$C_6$ olefins and paraffins were found in the recovered propylene, in addition to propylene, and so it was supposed that the eliminated isopropyl group was subjected to complicated side reactions such as oligomerization, cracking, hydrogenation, etc. Further, from the total carbon content of the $C_2$–$C_6$ volatile gases which was lower than that calculated from the eliminated isopropyl groups, it was supposed that some parts of the latter were changed to heavy components having more than six carbon atoms. Thus, these known methods had not only a defect that the percent recovery of the recovered olefins was very low but also a defect that the purity of the recovered olefins was low and, accordingly, separate olefin-purification equipments were required.

On the other hand, Japanese Patent Application (OPI) No. 103119/1981 discloses that when the reaction is carried out in the presence of an H-ZSM-5 catalyst while feeding a mixed cymene together with aniline or ammonia, the dealkylation proceeds with a high para-selectivity, whereby propylene is recovered in a high purity as 94%. However, this method also had the following defects: Namely, when an actual embodiment to be applied industrially is taken into account, while the recovered toluene and propylene are recycled into the alkylation region, it is necessary to separate the aniline or ammonia from the recovered toluene and propylene since the alkylating catalyst would be deactivated by a base such as the entraining aniline or ammonia, if any. Thus, the process cannot be said as economical one.

The present inventors have already proposed a method using a crystalline zeolite catalyst ion-exchanged with lithium ions, as a method for selective dealkylation at the para-position, which was improved in various defects of the above-described known methods (Japanese Patent Application (OPI) No. 216835/1984).

According to the above-proposed method, the dealkylation occurred selectively at the para-position, and recovered olefins can be obtained in a high percent recovery and a high purity. However, since the higher the degree of ion-exchange, the better the result, the preparation of the catalyst was not easy. On ion-exchanging a crystalline zeolite with lithium ions, it was not so easy to enhance the degree of ion-exchange, probably because the lithium ions were hydrated and their ionic radius was increased, and a special treatment such as a treatment at high temperatures was therefore required. Thus, the method using such a catalyst was not necessarily satisfactory on an industrial scale.

Furthermore, at that time the inventors believed that these specific effects of the lithium ions were characteristic for the lithium ions only, and other alkali metal ions such as sodium ion, potassium ion, rubidium ion, and cesium ion could not show such superior properties. But with a view to finding out a more excellent method for selective dealkylation at the para-position, the present inventors have made further investigations on various ion-exchanged zeolite catalysts and, as a result, found that the selective dealkylation at the para-position can be performed with equal or higher yield and purity of recovered olefins, using the zeolite catalyst ion-exchanged with a specified amount of a specific base ion (other than lithium ion), which can be prepared easily under very mild conditions unlike the catalyst ion-exchanged with lithium ions. The present invention has been thus accomplished.

SUMMARY OF THE INVENTION

The present invention provides an industrially excellent method for selectively dealkylating a 1,4-dialkylbenzene in a dialkylbenzene mixture by the use of, as the catalyst, a crystalline zeolite having a silica/alumina molar ratio of at least 12/1 and a constrained index of 1 to 12, modified with a metal or metalloid oxide, wherein the crystalline zeolite is ion-exchanged with a treatment liquor containing a base ion selected from the group consisting of sodium ion, potassium ion, rubidium ion, and cesium ion and contains the base ion in an atomic ratio of 0.5/1 to 1.0/1 with respect to aluminum.

DETAILED DESCRIPTION OF THE INVENTION

In the present invention, the dialkylbenzene to which the gist of the present invention can apply particularly advantageously is a compound containing a secondary and/or tertiary alkyl group having 3 to 12 carbon atoms. Specific examples of the 1,4-dialkylbenzene include, for example, 1-isopropyl-4-methylbenzene, 1,4-diisopropylbenzene, 1-sec-butyl-4-methylbenzene, 1-tert-butyl-4-methylbenzene, and the like. The effect of the present invention consists in not only the point that the 1,4-dialkylbenzene alone contained in the dialkylbenzene mixture can selectively be dealkylated and the formed olefin (e.g., propylene for 1-isopropyl-4-methylbenzene or isobutylene for 1-tert-butyl-4-methylbenzene) can be recovered in a high yield and a high purity, but also the point that the catalyst can be prepared very easily.

Consequently, by incorporating the method of the present invention after the usual alkylation step, the m-dialkyl isomer (or m- and o-dialkyl isomers) can be obtained easily in a high purity, and the benzenes and olefins produced by dealkylation can be recycled as such to the alkylation step, while the catalyst can be prepared easily. This method, therefore, becomes a very rational process.

Next, the method of the present invention will be illustrated specifically. The crystalline zeolite catalyst used in the present invention (hereinafter referred to as zeolite catalyst) is a zeolite having characteristics that the silica/alumina molar ratio is 12/1 or more and besides the constrained index (described later) is 1 to 12, and its typical example is those (pentacyl type zeolites) which were developed by Mobil Oil Co. or Union Carbide Corporation and are generally called "ZSM type zeolite" or "Silicalite".

The characteristic or ZSM type zeolite is to have a high silica/alumina molar ratio, and this molar ratio can be measured by the common analytical methods such as atomic absorption method.

The constrained index is defined by the following equation:

$$\text{Constrained index} = \frac{\log \text{(content of remaining hexane)}}{\log \text{(content of remaining 3-methylpentane)}}$$

This index shows a degree to which the channel of the zeolite crystal controls the access to itself of molecules having a section larger than that of n-paraffin. The specific measurement method is described in Japanese Patent Application (OPI) No. 133223/1981.

The value of this constrained index approaches the ratio of cracking rates of the both hydrocarbons.

A preferred zeolite for the present invention is one having a constrained index of 1 to 12. The constrained index of some typical zeolites is shown below:

|        | Constrained Index | Reference |
|--------|-------------------|-----------|
| ZSM-5  | 8.3 | Japanese Patent Publication No. 10064/1971 |
| ZSM-11 | 8.7 | Japanese Patent Publication No. 23280/1978 |
| ZSM-12 | 2   | Japanese Patent Publication No. 16079/1977 |
| ZSM-23 | 9.1 | Japanese Patent Application (OPI) No. 149900/1976 |
| ZSM-35 | 4.5 | Japanese Patent Application (OPI) No. 144500/1978 |
| ZSM-38 | 2   | U.S. Pat. No. 4,046,859 |
| ZSM-48 | 3.4 | Japanese Patent Application (OPI) No. 133223/1981 |

The value of the constrained index is the important critical definition of a useful zeolite in the present invention. Since, however, some latitude is allowed in the measurement method described above, the value sometimes varies with the measurement condition.

Consequently, the value of the constrained index is a mean value of those obtained under some different measurement conditions.

Thus the crystalline zeolite used according to the method of the present invention has been defined by the two values of silica/alumina molar ratio and constrained index. The above-mentioned ZSM type zeolites developed by Mobil Oil Co., such as ZSM-5, ZSM-11, ZSM-12, ZSM-23, ZSM-35, ZSM-38, and ZSM-48, are specific examples of the crystalline zeolite. The preparation method and the X-ray diffraction pattern of these ZSM type zeolites are described in the above-listed references, respectively.

Next, the ion-exchanging treatment with a base ion, which constitutes the most important point of the present invention, is explained. $H^+$-ZSM type zeolites show various acid strength distributions and acid amounts (the number of acid points) in accordance with their Si/Al ratios. As the result of minute investigations made by the present inventors, however, as the acid strength of the $H^+$-ZSM type zeolite used for dealkylation is high and the acid amount is large, side reactions of the olefins produced by the dealkylation occur more likely and the purity and yield of the olefins lower. Therefore, it is necessary to adjust the acid strength and/or the acid amount, in order to recover olefins having a high purity in a high yield. The present inventors have found that zeolite catalysts ion-exchanged with a specified amount of a specified base ion are effective for this purpose and, in addition, such zeolite catalysts can be prepared very easily.

Examples of the base ion used in the present invention include sodium ion, potassium ion, rubidium ion, and cesium ion, and its content in the zeolite catalyst is 0.5/1 to 1.0/1, preferably 0.7/1 to 1.0/1 in terms of atomic ratio with respect to aluminum in the zeolite skeleton. When the atomic ratio is higher than 1.0/1, the dealkylating activity of the catalyst lowers, whereas when the atomic ratio is lower than 0.5/1, the purity and yield of the recovered olefins lower remarkably.

The ion-exchanging treatment can be carried out in a usual method. That is, the ion-exchanging is effected easily even at room temperature by bringing a calcined ZSM type zeolite into contact with an aqueous solution of the above-mentioned base, followed by filtration and washing steps whereby the ion-exchanged zeolite as prescribed above can be obtained. As the source of the base ion, an alkaline compound in the form of a chloride, nitrate, bicarbonate, carbonate, phosphate, acetate, hydroxide, or the like, can be used alone or in combination. Although it is particularly preferred to use a hydroxide in combination with salt, an excessively high pH region where the zeolite crystal might be dissolved must be avoided.

After the ion-exchanging operation, washing with distilled water is carried out sufficiently to remove any matter adhering or remaining on the surface of zeolite.

The degree of ion-exchanging with base ions can be measured by a chemical elemental analysis such as the atomic absorption method, or the like.

Next, the modification method for the ZSM type zeolite with a metal or metalloid oxide, which is a means used in the method of the present invention in combination with the ion-exchanging treatment with base ions, is explained. In this modification method, a ZSM type zeolite is dipped in a solution containing a metal or metalloid compound, and the solution is concentrated (in some cases, a filtration process is included). Thereafter, the zeolite on which the metal or metalloid compound is supported is calcined at a temperature of 400° to 600° C. in a stream of air, whereby the ZSM type zeolite is modified with the metal or metalloid in the form of oxide. It is supposed that, by the two effects of such modification method, i.e., poisoning of the acid sites of the surface outside the channels of the ZSM type zeolite and some narrowing of the entrances of the channels, only the acid sites in the channels of the resulting ZSM type zeolite act effectively, and the so-called para-selectivity appears (in other words, only a p-isomer among the dialkylbenzenes is dealkylated selectively).

The modification treatment may be carried out either before or after the above-mentioned ion-exchanging treatment with a base ion ($M^+$). When the modification treatment is carried out after the ion-exchanging treatment with a base ion, however, it is necessary to perform the modification treatment quickly such that any re-exchanging of $M^+$ ion does not occur.

In the modification method specifically disclosed by the examples described below, the following procedure is employed: $M^+$-ZSM-5 is dipped in an aqueous magnesium acetate solution, and after concentrating the solution, the solution is calcined for 3 hours at 500° C. in a stream of air, whereby $M^+$-ZSM-5 modified with MgO is obtained. Such procedure is one of many combinations of the processes.

The methods per se which are used in the present invention for the modification with a metal or metalloid oxide are known. For example, the method by the present inventors (Japanese Patent Application No. 44241/1982), the methods by Mobil Oil Co. (Japanese Patent Application (OPI) Nos. 133030/1981, 133031/1981, 133032/1981, 133223/1981, 144750/1981, 145227/1981, 10337/1982, etc.), and others are known. In the method of the present invention, the characteristic resides in the point of using the known modification method in combination with the above-mentioned ion-exchanging treatment with a base ion.

The metal or metalloid compound for modifying the ZSM type zeolite is a compound of at least one element selected from the group consisting of the lanthanum elements (e.g., La, Ce, and Nd), the group IIa elements (Ba, Mg, and Sr), the group IIb elements (e.g., Zn and Cd), the group IIIa elements (e.g., Ga and IN), the group IVa elements (e.g., Ge, Sn, and Pb), the group Va elements (e.g., P), the group VIa elements (e.g., Te), the group VIb elements (e.g., Cr, Mo, and W), and the group VIIb elements (e.g., Mn and Re).

This metal compound or metalloid compound is mixed with the ZSM type zeolite in the form of a solution, and through the steps of concentration and calcination, it finally modifies the ZSM type zeolite catalyst in the form of, substantially, a metal oxide or metalloid oxide. Examples of a suitable solvent used in this case include, for example, water, aromatic or aliphatic hydrocarbons, alcohols, organic acids (e.g., formic acid, acetic acid, and propionic acid), and inorganic acids (e.g., hydrochloric acid, nitric acid, and sulfuric acid). Alternatively, halogenated hydrocarbons, ketones, ethers, etc. also are useful. Of these solvents, water is used most commonly. The ZSM type zeolite is dipped in this solution, and after concentration, it is dried, but in some cases, it is filtered after dipping and then dried. Drying is carried out at a temperature of generally 80° C. to 150° C. Calcination after drying is carried out at a temperature of 300° C. or higher, preferably 400° to 550° C. for several hours in an air stream. The amount of the metal or metalloid oxide modifying the ZSM type zeolite after calcination is selected from a range of from 1 wt% to 50 wt%.

The dealkylation reaction of dialkylbenzenes is carried out by bringing the dialkylbenzene mixture into contact with the ZSM type zeolite catalyst modified with the above-mentioned metal or metalloid oxide. The catalytic system of the present invention may be used alone but it is usually put into practical uses after diluting with a binder such as alumina and press molding.

The dealkylation is mainly carried out by the gas-phase catalytic reaction. In this reaction, inert gases such as nitrogen, helium, argon, etc. may be used as a diluent. The use of the diluent is employed, in some cases, for the purpose of positively aiming to control the occurrence of side reactions by dilution of the substrate, to thereby keep the purity of the recovered olefin high.

The reaction temperature cannot be determined simply because it is affected by the kind of alkyl groups to be dealkylated, but generally it is selected from a range of from 250° to 600° C. The alkyl group which is an object of dealkylation of the present invention is a secondary and/or tertiary alkyl group having 3 to 12 carbon atoms. Generally, however, the progress of the dealkylation becomes easy as an increase in the number of carbon atoms of the alkyl group, or it is easier in tertiary alkyl groups than in secondary ones. The reaction temperature, therefore, shifts to a low temperature side.

One characteristic of the present catalytic system is that, even if the dealkylation is carried out at high temperatures in order to raise the dealkylation rate, the selectivity to the dealkylation of the 1,4-isomer is kept high (in other words, both the 1,2- and 1,3-isomers are left completely or nearly unreacted) and besides both the purity and percent recovery of the recovered olefin are also kept high.

The contact time is selected from a range of from 0.1 to 60 seconds, preferably from 1 to 30 seconds.

Another characteristic of the present catalytic system is that, even if the dealkylation is carried out for a long contact time in order to raise the dealkylation rate, the selectivity to the dealkylation of the 1,4-isomer as well as the percent recovery and purity of the recovered olefin are kept high.

A further characteristic of the present catalytic system is that the catalytic system has a long life, and reduction in the catalytic activity due to deposition of carbonaceous substances is very little even in a prolonged reaction.

The dealkylation of the present invention is carried out using a fixed-bed or fluidized-bed catalytic system according to a batchwise, semi-continuous, or continuous process. In either case, for the regeneration of the catalyst, carbonaceous substances on the catalyst are burned out at a temperature of about 500° C. to 550° C. using an inert gas containing a little oxygen (0.5 to 2.0%).

The present invention will be illustrated in more detail with reference to the following specific examples, but it is not to be interpreted as being limited thereto.

The reaction results in the examples were calculated by means of the following equations.

Total conversion (%) =

$$\left(1 - \frac{\text{unreacted dialkylbenzene (mole)}}{\text{starting dialkylbenzene (mole)}}\right) \times 100$$

Conversion of p-isomer (%) =

$$\left(1 - \frac{\text{unreacted p-dialkylbenzene (mole)}}{\text{starting p-dialkylbenzene (mole)}}\right) \times 100$$

-continued

Yield of monoalkylbenzene (%) =

$$\frac{\text{formed monoalkylbenzene (mole)}}{\text{starting dialkylbenzene (mole)}} \times 100$$

Yield of olefin (%) (1) = $\frac{\text{formed olefin (1) (mole)}}{\text{starting dialkylbenzene (mole)}} \times 100$ Percent recovery of m-isomer (%) =

$$\frac{\text{unreacted m-dialkylbenzene (mole)}}{\text{starting m-dialkylbenzene (mole)}} \times 100$$

Percent recovery of o-isomer (%) =

$$\frac{\text{unreacted o-dialkylbenzene (mole)}}{\text{starting o-dialkylbenzene (mole)}} \times 100$$

Percent recovery of aromatic substance (%) =

$$\frac{\text{recovered alkylbenzenes (mole)}}{\text{starting dialkylbenzene (mole)}} \times 100$$

Percent recovery of gas (%) =

$$\frac{\text{recovered gas (2) (carbon, g-atom)}}{\text{eliminated alkyl group (carbon, g-atom)}} \times 100$$

Purity of olefin (%) (1) = $\frac{\text{formed olefin (1) (mole)}}{\text{recovered gas (2) (mole)}} \times 100$ (1): An objective main olefin formed by dealkylation (e.g., propylene for cymene and isobutylene for tert-butyltoluene).
(2): Total $C_1$–$C_6$ volatile olefins and paraffins.

The analysis of the reaction products was carried out by gas chromatography.

REFERENTIAL EXAMPLE 1

Synthesis of ZSM-5:

Starting solutions each having the following formulation were first prepared.

| Solution A | |
| --- | --- |
| Water | 162 g |
| $H_2SO_4$ | 16.7 g |
| $Al_2(SO_4)_3 \cdot 17H_2O$ | 1.46 g |
| $(n\text{-}C_3H_7)_4NBr$ | 20.3 g |
| Solution B | |
| Water | 119.7 g |
| Sodium silicate (Grade No. 3) | 186.3 g |
| Solution C | |
| Water | 281.7 g |
| NaCl | 70.9 g |

The solutions A and B were dropped to the solution C at the same time and then mixed. At this time, the mixture was vigorously stirred while maintaining the pH at 9 to 11 (for this pH adjustment, 6.0 g of a 48% aqueous NaOH solution was added). The pH when the mixing was completed was 9.55. The mixture was placed in a 1-liter SUS autoclave and then was subjected to a hydrothermal reaction while stirring at 160° C. for 20 hours (N=350 to 400 rpm). After being cooled, the reaction mixture was filtered and thoroughly washed with a large amount (up to 7 liters) of distilled water. In this manner, the washing/filtration cycle was repeated. The reaction product was dried at 120° C. for 15 hours and then calcined at 530° C. for 3 hours in an air stream to yield 47.5 g of white powdery crystals (yield=84.6%).

The X-ray diffraction analysis confirmed that the product was ZSM-5. The degree of crystallinity was 93.2%. The fluorescent X-ray analysis showed that the $SiO_2/Al_2O_3$ molar ratio was 64.0/1. Next, the Na/H type ZSM-5 thus obtained was ion-exchanged three times with each 200 g of a 5% aqueous ammonium chloride solution at 65° C. for 2 hours, and then further ion-exchanged with 200 g of a 5% aqueous ammonium chloride solution at 25° C. for one night. After the filtration, the residue was washed five times in total with 200 g of distilled water and then dried at 120° C. for 10 hours to give 38 g of $NH^+_4$ type ZSM-5.

REFERENTIAL EXAMPLES 2 to 3

Synthesis of ZSM-5:

The amount of aluminum sulfate in Referential Example 1 was changed to prepare ZSM-5s having various $SiO_2/Al_2O_3$ molar ratios. During the mixing of the solutions A, B, and C, the pH was maintained at 9 to 11, and the pH after completion of the mixing was adjusted to 9 to 10. For this pH adjustment, caustic soda was used. The results obtained are shown in Table 1.

TABLE 1

| Referential Example No. | Amount (g) | Yield (%) | Crystal Form | Degree of Crystallinity (%) | $SiO_2/Al_2O_3$ Molar Ratio |
|---|---|---|---|---|---|
| 1 | 47.5 | 84.6 | ZSM-5 | 93.2 | 64.0/1 |
| 2 | 50.2 | 83.1 | " | 50.5 | 15.2/1 |
| 3 | 46.1 | 85.9 | " | 100.0 | 254/1 |

Next, each of the Na/H type ZSM-5s thus obtained was ion-exchanged according to the process as described in the latter half of Referential Example 1 to change into $NH^+_4$ type ZSM-5.

CATALYST PREPARATION EXAMPLE 1

Ion-exchanging with Na ion and modifying with MgO:

Ion-exchanging treatment was carried out by dispersing 4.0 g of the $NH^+_4$ type ZSM-5 having an $SiO_2/Al_2O_3$ molar ratio of 64.0/1 as obtained in Referential Example 1 in 140 ml of an ion-exchanging liquor consisting of 2 parts of an aqueous 0.1 mole/liter NaCl solution and 1 part of an aqueous 0.1N NaOH solution (Na ion amount in the ion-exchanging liquor per Al atom in ZSM-5 (Na/Al)=6.8/1) and stirring the dispersion at room temperature for 1 hour. After the filtration, the residue was well washed with distilled water and then dried at 120° C. for 2 hours to give $Na^+$-ZSM-5. The Na/Al ratio of the catalyst was 0.95/1.

Next, 28 ml of an aqueous 8 wt% magnesium acetate solution was added to 2.5 g of the $Na^+$-ZSM-5 thus obtained, and then stirred. The dispersion was concentrated at 80° C. under reduced pressure to dryness. Subsequently, the residue was dried at 120° C. for 10 hours and calcined at 530° C. in an air stream for 3 hours to give 3.1 g of $MgO-Na^+$-ZSM-5 (amount of MgO for modification: 20 wt%).

EXAMPLE 1

Catalytic activity test by fixed-bed flow reaction:

Dealkylation of cymene using an ordinary atmospheric pressure fixed-bed flow reactor was carried out as follows:

In a quartz glass tubular reactor having a length of 32 cm and an inside diameter of 1 cm was charged 1 g of the 20 wt% $MgO-Na^+$-ZSM-5 catalyst prepared in Catalyst Preparation Example 1 (the catalyst was crushed after pressure molding, and arranged to have a particle diameter of 24 to 48 mesh), and the catalyst was preheated at 400° C. for 1 hour in a nitrogen stream. Then, cymene (m/p/o=63.6/32.9/3.5) was fed to the reactor at a WHSV (weight hourly space velocity) of 2.7 $hr^{-1}$ and reacted. The temperature of the catalyst bed (the reaction temperature) was varied stepwise from 350° C. to 450° C. The reaction product was collected by trapping by ice-cooling, and the aromatic component was analyzed by gas chromatography. The volatile gas component was analyzed by introducing the mixed reaction gas directly into a gas chromatographic column. The results obtained are shown in Table 2.

CATALYST PREPARATION EXAMPLE 2

With each of the two $NH^+_4$-ZSM-5s obtained in Referential Examples 1 and 2 having different $SiO_2/Al_2O_3$ molar ratios, the ion-exchanging treatment with Na ion was effected according to the manner as described in Catalyst Preparation Example 1. At that time, the treatment was carried out by suitably varying the amount of the ion-exchanging liquor. After the filtration and washing, $Na^+$-ZSM-5 was obtained.

Next, with each of the $Na^+$-ZSM-5s, the treatment for supporting 20 wt% MgO was effected according to the manner as described in Catalyst Preparation Example 1. The catalysts thus obtained are shown in Table 2.

TABLE 2

| Catalyst No. | $SiO_2/Al_2O_3$ Molar Ratio | Na/Al Ratio on Ion-Exchanging | Na/Al Ratio of Catalyst | Catalyst Preparation Example No. |
|---|---|---|---|---|
| 1 | 64.0/1 | 6.8/1 | 0.95/1 | 1 |
| 2 | " | 3.8/1 | 0.79/1 | 2 |
| 3 | " | 4.5/1 | 0.84/1 | 2 |
| 4 | " | 1.0/1 | 0.31/1 | 2 |
| 5 | " | 10.0/1 | 1.25/1 | 2 |
| 6 | 15.2/1 | 5.9/1 | 0.94/1 | 2 |

EXAMPLE 2

Dealkylation of cymene was carried out according to the manner as described in Example 1, using each of the catalyst Nos. 2, 3 and 6 obtained in Catalyst Preparation Example 2.

The results obtained in shown in Table 3.

COMPARATIVE EXAMPLES 1 AND 2

Dealkylation of cymene was carried out according to the manner as described in Example 1, using each of the Catalyst Nos. 4 and 5 obtained in Catalyst Preparation Example 2.

The results obtained are shown in Table 3.

TABLE 3

| Example No. | Catalyst No. | SiO$_2$Al$_2$O$_3$ Molar Ratio | Na/al Ratio of Catalyst | Reaction Temperature (°C.) | Conversion % p-Cymene | Conversion % Total Cymene | Yield (%) Toluene | Yield (%) Propylene | Percent Recovery of m-Cymene (%) | Purity of Propylene (%) |
|---|---|---|---|---|---|---|---|---|---|---|
| Example 2 | 1 | 64.0/1 | 0.95/1 | 350 | 15.3 | 4.7 | 5.3 | 5.1 | 100 | 100 |
| " | 3 | " | 0.84/1 | " | 28.6 | 10.1 | 10.4 | 9.7 | " | 99.6 |
| " | 2 | " | 0.79/1 | " | 54.2 | 18.0 | 18.4 | 15.9 | " | 92.3 |
| " | 6 | 15.2/1 | 0.94/1 | " | 21.2 | 9.5 | 6.9 | 5.3 | 98.4 | 93.8 |
| " | 1 | 64.0/1 | 0.95/1 | 450 | 61.9 | 21.4 | 21.5 | 20.9 | 100 | 99.2 |
| " | 2 | " | 0.79/1 | " | 91.0 | 33.6 | 32.3 | 25.2 | 98.8 | 72.8 |
| Comparative Example 1 | 4 | " | 0.31/1 | 350 | 97.2 | 34.9 | 34.0 | 8.7 | 97.5 | 29.8 |
| Comparative Example 2 | 5 | " | 1.25/1 | " | <Dealkylation reaction hardly proceeded.> | | | | | |

CATALYST PREPARATION EXAMPLE 3

Using 3.0 g each of the NH$^+_4$-ZSM-5s obtained in Referential Example 3 having an SiO$_2$/Al$_2$O$_3$ molar ratio of 254/1, the following treatments were carried out:

(1) Ion-exchanging treatment was carried out by dispersing 3.0 g of NH$^+_4$-ZSM-5 into a mixed aqueous solution (90 ml) consisting of 60 ml of an aqueous 0.015 mole/liter NaCl solution and 30 ml of an aqueous 0.015 mole/liter NaOH solution and stirring the dispersion at room temperature for 1 hour. After the filtration, washing and drying, Na$^+$-ZSM-5 was obtained.

Next, the treatment for modifying with MgO was effected according to the manner as described in Catalyst Preparation Example 1 to give 20 wt% MgO-modified type Na$^+$-ZSM-5.

(2) Ion-exchanging treatments with K ion, Rb ion, and Cs ion were effected according to the above treatment (1), using a mixed aqueous solution of KCl/KOH, a mixed aqueous solution of RbCl/RbOH, and a mixed aqueous solution of CsCl/CsOH, respectively. Subsequent treatment for modifying with MgO gave the following 20 wt% MgO-modified catalysts.

(3) The NH$^+_4$-ZSM-5 was converted into H$^+$-ZSM-5 by subjecting to calcination in an air stream at 530° C. for 3 hours without effecting any ion-exchanging treatment. Through the treatment for modifying with MgO as described in the latter half of Catalyst Preparation Example 1, the following 20 wt% MgO-modified H$^+$-ZSM-5 catalyst was obtained.

TABLE 4

| Catalyst No. | Ion M$^+$ | M/Al Ratio of Catalyst |
|---|---|---|
| 7 | Na | 0.85/1 |
| 8 | K | 0.82/1 |
| 9 | Rb | 0.80/1 |
| 10 | Cs | 0.76/1 |
| 11 | H | — |

EXAMPLE 3

Using each of the Catalyst Nos. 7, 8, and 9 obtained in Catalyst Preparation Example 3, dealkylation of cymene was carried out according to the manner as described in Example 1. The reaction temperature employed was 350° C. The results obtained are shown in Table 5.

COMPARATIVE EXAMPLE 3

Using the Catalyst No. 11 obtained in Catalyst Preparation Example 3, dealkylation of cymene was carried out in the same manner as described in Example 3. The results obtained are shown in Table 5.

TABLE 5

| Example No. | Catalyst No. | Catalyst | Conversion (%) p-Cymene | Conversion (%) Total Cymene | Yield (%) Toluene | Yield (%) Propylene | Percent Recovery of m-Cymene (%) | Purity of Propylene (%) |
|---|---|---|---|---|---|---|---|---|
| Example 3 | 7 | MgO—Na$^+$—ZSM-5 | 44.1 | 14.9 | 15.4 | 13.3 | 100 | 91.0 |
| " | 8 | MgO—K$^+$—ZSM-5 | 34.5 | 12.4 | 11.8 | 11.0 | 98.0 | 99.0 |
| " | 9 | MgO—Rb$^+$—ZSM-5 | 25.5 | 9.0 | 8.4 | 7.8 | 99.0 | 99.5 |
| " | 10 | MgO—Cs$^+$—ZSM-5 | 19.0 | 6.8 | 6.5 | 6.9 | 99.0 | 100 |
| Comparative Example 3 | 11 | MgO—H$^+$—ZSM-5 | 97.9 | 35.3 | 31.3 | 2.5 | 97.8 | 16.4 |

While the invention has been described in detail and with reference to specific embodiments thereof, it will be apparent to one skilled in the art that various changes and modifications can be made therein without departing from the spirit and scope thereof.

What is claimed is:

1. A method for selectively dealkylating a 1,4-dialkylbenzene in a dialkylbenzene mixture in the presence of, as a catalyst, a crystalline zeolite having an SiO$_2$/Al$_2$O$_3$ molar ratio of at least 12/1 and a constrained index of 1 to 12, modified with a metal or metalloid oxide, wherein the crystalline zeolite is ion-exchanged with a treatment liquor containing a base ion selected from the group consisting of sodium ion, potassium ion, rubidium ion, and cesium ion and contains the base ion in an atomic ratio of 0.5/1 to 1.0/1 with respect to aluminum.

2. A method as claimed in claim 1, wherein the base ion is contained in an atomic ratio of 0.7/1 to 1.0/1 with respect to aluminum.

3. A method as claimed in claim 1, wherein at least one alkyl group of the 1,4-dialkylbenzene is a secondary or tertiary alkyl group having 3 to 12 carbon atoms.

4. A method as claimed in claim 1, wherein the 1,4-dialkylbenzene is 1-isopropyl-4-methylbenzene, 1,4-diisopropylbenzene, 1-sec-butyl-4-methylbenzene, or 1-tert-butyl-4-methylbenzene.

5. A method as claimed in claim 1, wherein the crystalline zeolite is ZSM-5, ZSM-11, ZSM-12, ZSM-23, ZSM-35, ZSM-38, or ZSM-48.

6. A method as claimed in claim 1, wherein the metal or metalloid oxide modifying the crystalline zeolite is an oxide of at least one element selected from the group consisting of La, Ce, and Nd of the lanthanum group; Ba, Mg, and Sr of the group IIa; Zn and Cd of the group IIb; Ga and In of the group IIIa; Ge, Sn, and Pb of the group IVa; P of the group Va; Te of the group VIa, Cr, Mo, and W of the group VIb; and Mn and Re of the group VIIb.

7. A method as claimed in claim 1, wherein the crystalline zeolite is ZSM-5, and the metal oxide modifying it is magnesium oxide.

* * * * *